United States Patent [19]
Fisher

[11] Patent Number: 5,771,713
[45] Date of Patent: Jun. 30, 1998

[54] CRYOGENIC RECTIFICATION SYSTEM FOR RECOVERY OF FLUORINE COMPOUNDS

[75] Inventor: Theodore Fringelin Fisher, Amherst, N.Y.

[73] Assignee: Praxair Technology, Inc., Danbury, Conn.

[21] Appl. No.: 914,788

[22] Filed: Aug. 20, 1997

[51] Int. Cl.$^6$ ............................................. F25J 1/00
[52] U.S. Cl. .............................................. 62/625; 62/918
[58] Field of Search ...................................... 62/625, 918

[56] References Cited

U.S. PATENT DOCUMENTS

| | | | |
|---|---|---|---|
| 3,620,030 | 11/1971 | Iikubo et al. | 62/918 |
| 4,162,272 | 7/1979 | Vautrain | 62/918 |
| 5,502,969 | 4/1996 | Jin et al. | 62/11 |
| 5,626,023 | 5/1997 | Fisher et al. | 62/625 |

*Primary Examiner*—Ronald C. Capossela
*Attorney, Agent, or Firm*—Stanley Ktorides

[57] ABSTRACT

A cryogenic system for the recovery of fluorine compounds from a carrier gas stream such as an effluent stream from a semiconductor facility comprising three cryogenic rectification columns and a mass transfer contacting device.

8 Claims, 2 Drawing Sheets

5,771,713

CRYOGENIC RECTIFICATION SYSTEM FOR RECOVERY OF FLUORINE COMPOUNDS

TECHNICAL FIELD

This invention relates to the recovery of fluorine compounds employing cryogenic rectification. It is particularly useful for recovering fluorine compounds from an effluent of a semiconductor production facility.

BACKGROUND ART

Fluorine compounds are used in many manufacturing processes. In particular, they are widely used in the manufacture of semiconductors. Fluorine compounds are among the more costly of the more commonly used chemicals in manufacturing processes and, moreover, are among the more environmentally detrimental of such chemicals. Accordingly there is a need for recovering fluorine compounds used in manufacturing processes so that they not cause environmental problems and also so that they may be reused.

One method currently used by industry for ensuring that fluorine compounds are not released to the environment involves combustion of the fluorine compounds contained in an effluent stream. While this method effectively destroys the fluorine compounds thus preventing environmental pollution, it also makes it impossible to reuse the fluorine compounds. This method is also disadvantageous because it generates waste gases such as hydrogen fluoride and nitrogen oxides which require further treatment. Furthermore, combustion processes require fuel and oxidant to operate, adding further operating and capital costs to the manufacturing operation.

Another method currently used by industry for the recovery of fluorine compounds is adsorption wherein the fluorine compounds are adsorbed onto adsorbent under elevated pressure and desorbed from the adsorbent under vacuum. This method is disadvantageous because very high power consumption is needed to carry out the requisite pressurization and depressurization. Moreover, the fluorine compound mixture from the desorption generally requires further purification before the components of the mixture can be reused. Still further, adsorption processes do not have the flexibility to deal with the dramatic changes in fluorine compound concentrations and flow rates which characterize manufacturing effluent streams such as those from a semiconductor manufacturing plant.

A recent significant advancement in the field of fluorine compound recovery is disclosed and claimed in U.S. Pat. No. 5,502,969 — Jin et al. In this system a wash liquid system is used with a cryogenic rectification system to separate fluorine compounds from a carrier gas. While this system is very effective, it requires the use of a large amount of wash liquid and has a high level of energy consumption. Moreover, it provides for the direct recovery of only a small number of fluorine compounds. If separate recovery of a large number of different fluorine compounds is desired, further processing is necessary.

Accordingly it is an object of this invention to provide an improved fluorine compound recovery system using cryogenic rectification.

SUMMARY OF THE INVENTION

The above and other objects which will become apparent to those skilled in the art upon a reading of this disclosure are attained by the present invention one aspect of which is:

A method for recovering fluorine compounds comprising:

(A) passing gaseous feed comprising carrier gas and high volatility fluorine compounds into a mass transfer contacting device, and passing wash liquid into the mass transfer contacting device;

(B) passing high volatility fluorine compounds into the wash liquid within the mass transfer contacting device to produce vapor comprising carrier gas and wash liquid comprising high volatility fluorine compounds;

(C) passing the wash liquid comprising high volatility fluorine compounds into a first rectification column as first column feed and separating the first column feed within said first rectification column by cryogenic rectification into top fluid comprising high volatility fluorine compounds and first column bottom fluid;

(D) passing first column bottom fluid into a second rectification column as second column feed; separating the second column feed by cryogenic rectification into second column top fluid and into second column bottom fluid, and passing second column top fluid into the mass transfer contacting device as wash liquid;

(E) passing top fluid comprising high volatility fluorine compounds into a third rectification column as third column feed and separating the third column feed by cryogenic rectification into third column top vapor and product high volatility fluorine compounds; and (F) recovering high volatility fluorine compounds from the third rectification column.

Another aspect of the invention is:

Apparatus for the recovery of fluorine compounds comprising:

(A) a mass transfer contacting device and means for passing fluorine compound-containing feed into the mass transfer contacting device;

(B) a first rectification column and means for passing fluid from the mass transfer contacting device into the first rectification column;

(C) a second rectification column and means for passing fluid from the lower portion of the first rectification column into the second rectification column;

(D) means for passing fluid from the upper portion of the second column into the mass transfer contacting device;

(E) a third rectification column and means for passing fluid from the upper portion of the first rectification column into the third rectification column; and (F) means for recovering fluorine compound product from the upper portion of the third rectification column.

As used herein the term "fluorine compounds" means one or more compounds comprising fluorine.

As used herein the term "high volatility fluorine compounds" means one or more fluorine compounds having a normal, atmospheric pressure, boiling point below that of the wash liquid. In the case of the preferred wash liquid, this temperature is 236.5K. Examples include carbon tetrafluoride ($CF_4$), nitrogen trifluoride ($NF_3$), hexafluoroethane ($C_2F_6$), floroform ($CHF_3$), methyl fluoride ($CH_3F$), pentafluoroethane ($C_2HF_5$) and sulfur hexafluoride ($SF_6$).

As used herein the term "low volatility fluorine compounds" means one or more fluorine compounds which are not high volatility fluorine compounds. Examples include octafluorocyclobutane ($C_4F_8$). Low volatility fluorine compounds may include excess wash liquid fluid when that component is present in the feed stream.

As used herein the term "wash column" means a trayed or packed column in which a gas mixture is contacted with a liquid for the purpose of preferentially dissolving one or more components of the gas to provide a solution of them in the liquid. The operation is also known as gas absorption.

As used herein the term "rectification column" means a distillation or fractionation column or zone, i.e., a contacting column or zone wherein liquid and vapor phases are countercurrently contacted to effect separation of a fluid mixture, as for example, by contacting of the vapor and liquid phases on a series of vertically spaced trays or plates mounted within the column and/or on packing elements such as structured or random packing. For a further discussion of rectification columns, see the Chemical Engineer's Handbook, fifth edition, edited by R. H. Perry and C. H. Chilton, McGraw-Hill Book Company, New York Section 13, *The Continuous Distillation Process*.

Vapor and liquid contacting separation processes depend on the difference in vapor pressures for the components. The high vapor pressure (or more volatile or low boiling) component will tend to concentrate in the vapor phase whereas the low vapor pressure (or less volatile or high boiling) component will tend to concentrate in the liquid phase. Partial condensation is the separation process whereby cooling of a vapor mixture can be used to concentrate the volatile component(s) in the vapor phase and thereby the less volatile component(s) in the liquid phase. Rectification, or continuous distillation, is the separation process that combines successive partial vaporizations and condensations as obtained by a countercurrent treatment of the vapor and liquid phases. The countercurrent contacting of the vapor and liquid phase is generally adiabatic and can include integral (stagewise) or differential (continuous) contact between the phases. Separation process arrangements that utilize the principles of rectification to separate mixtures are often interchangeably termed rectification columns, distillation columns, or fractionation columns. Cryogenic rectification is a rectification process carried out at least in part at temperatures at or below 150 degrees Kelvin.

As used herein the term "indirect heat exchange" means the bringing of two fluid streams into heat exchange relation without any physical contact or intermixing of the fluids with each other.

As used herein "upper portion" and "lower portion" of a column mean those sections of a column respectively above and below the midpoint of the column.

DETAILED DESCRIPTION

The invention will be described in detail with reference to the Drawings.

Figure 1:
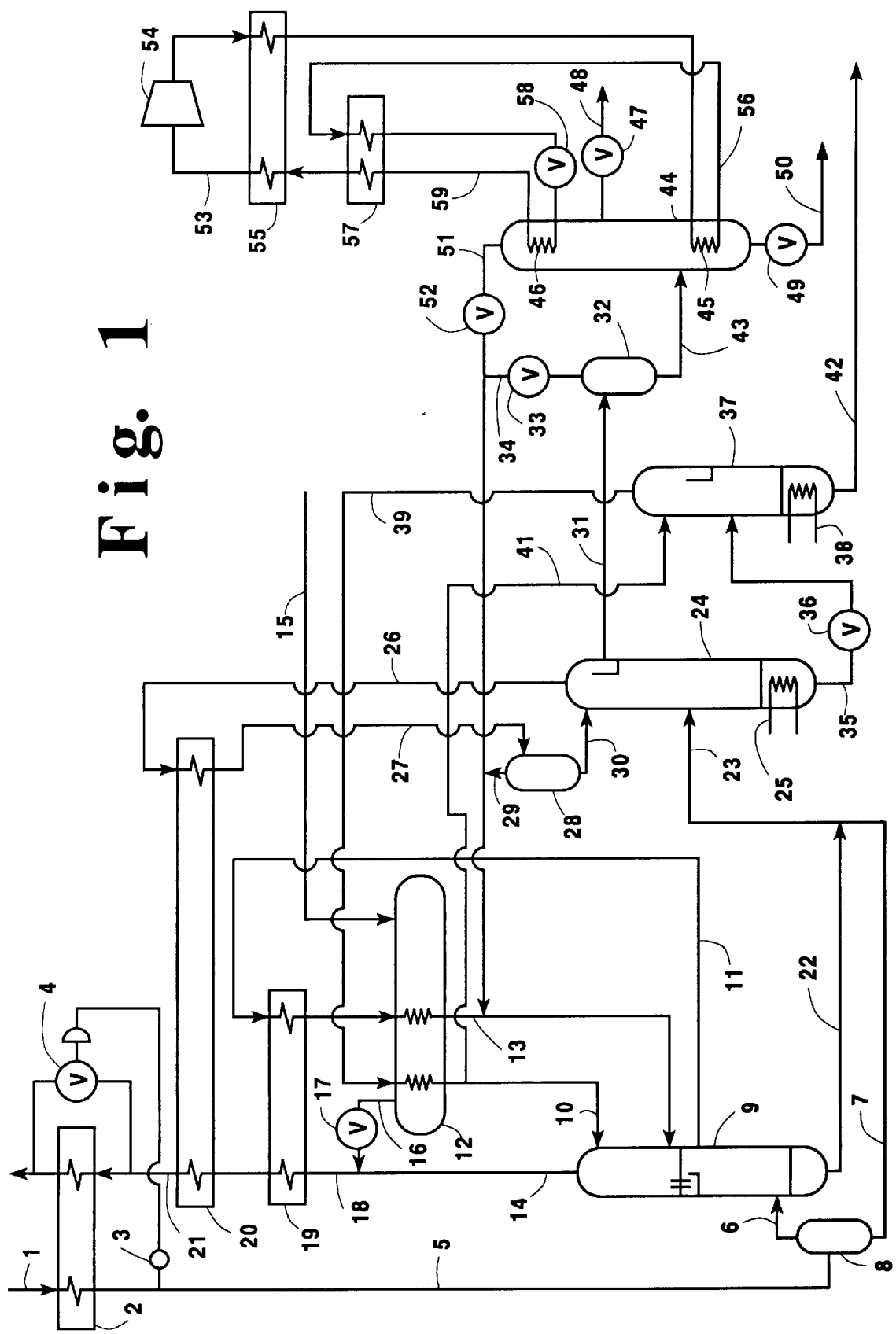
FIG. 1 is a schematic flow diagram of a preferred embodiment of the fluorine compound recovery system of this invention.

Referring now to FIG. 1, gaseous feed 1 which has been pressurized to a pressure of at least 18 and preferably at least 20 pounds per square inch absolute (psia) and has been treated to remove particulate and chemically active impurities such as hydrogen fluoride, silane, carbon dioxide and water, comprises nitrogen carrier gas and high volatility fluorine compounds. Gaseous feed 1 may also contain low volatility fluorine compounds. The invention will be described in detail with reference to the embodiment wherein gaseous feed 1 does contain low volatility fluorine compounds. The carrier gas of the gaseous feed may comprise other gases in addition to or in place of nitrogen such as oxygen, argon, helium and/or hydrogen. Feed 1 is cooled by indirect heat exchange in heat exchanger 2, with return carrier gas-containing top vapor taken from the wash column, to a temperature approximating that at which some of the fluorine compounds would begin to condense, either as solid or liquid. Generally such temperature is within the range of from 190° to 130° K. Temperature controller 3 controls valve 4 to ensure that the temperature of cooled feed 5 is within the desired range.

Some condensation of cooled feed 5 may be permitted to occur provided this will not result in solidification of any of its constituents. The stream may then be separated into gaseous fraction 6 and liquid fraction 7 in phase separator 8. Cooled gaseous feed or feed fraction 6 is then passed into the lower portion of wash column 9. Wash liquid 10 is passed into the upper portion of wash column 9. Wash liquid 10 has a freezing point lower than the temperature of the gaseous feed as it enters wash column 9 and has a vapor pressure at the temperature less than 1.0 mmHg and preferably less than 0.01 mmHg. A preferred wash liquid is perfluoropropane ($C_3F_8$). Other fluids which may be used as wash liquid 10 include propane, ethane and mixtures thereof.

The gaseous feed flows up wash column 9 and the wash liquid flows down wash column 9 and in the process high volatility fluorine compounds and, if present, low volatility fluorine compounds pass from the gaseous feed into the downflowing wash liquid to produce carrier gas-containing top vapor and wash liquid comprising high volatility and low volatility fluorine compounds. In the embodiment illustrated in FIG. 1 upflowing gas, which has been partially depleted of fluorine compounds, is withdrawn from wash column 9 as stream 11 and cooled by indirect heat exchange in heat exchanger 12. Resulting cooled stream 13 which may contain some liquid, is passed into wash column 9. The gas then continues up the wash column in countercurrent contact with the descending wash liquid to continue carrying out the aforesaid mass transfer of the fluorine compounds into the wash liquid. The carrier gas-containing vapor is withdrawn from the upper portion of wash column 9 as stream 14.

Liquid cryogen such as nitrogen stream 15 is supplied to heat exchanger 12, where it is vaporized to provide cooling of other process streams. The resultant gaseous nitrogen stream 16 is passed through valve 17, and then combined with stream 14 to comprise stream 18, which is passed through heat exchangers 19 and 20. The resultant stream 21 is passed, at least in part, through heat exchanger 2 to carry out the aforementioned cooling of gaseous feed 1 and is then passed out of the system. Alternatively, streams 14 and 16 may be maintained as separate streams, which are each passed through heat exchangers 19 and 20, and passed, at least in part, through heat exchanger 2, before being passed out of the system. Wash liquid comprising high and low volatility fluorine compounds as well as some dissolved carrier gas is withdrawn from the lower portion of wash column 9 as stream 22 and combined with cooled feed liquid fraction 7, if any, to comprise stream 23. The combined stream is supplied as column feed into the midportion of first rectification column 24, which is driven by external heat input through heat input line 25.

Within first rectification column 24 the first column feed is separated by cryogenic rectification into top fluid comprising high volatility fluorine compounds and carrier gas, and into first column bottom fluid. If low volatility fluorine compounds are present in first column feed 23, the first column bottom fluid comprises low volatility fluorine compounds. Some top fluid is withdrawn from the upper portion of first rectification column 24 as stream 26 and passed through heat exchanger 20. Resulting partially condensed stream 27 is then passed into phase separator 28. Vapor, comprised primarily of carrier gas is passed out from phase separator 28 in stream 29, and combined with stream 13 and then into wash column 9. Liquid is withdrawn from phase separator 28 as stream 30, and passed into the upper portion of first rectification column 24 as reflux.

Another portion of the top fluid comprising high volatility fluorine compounds is removed as liquid stream 31 from the section of first rectification column 24 above the feed point of the column, preferably from a point somewhat below that from which top vapor stream 26 is removed, and passed into batch storage tank 32, where it is stored for subsequent batch-wise processing in third column 44. The use of tank 32 is advantageous when there is significant variance in the fluorine compound concentration in the gaseous feed and/or in the gaseous feed flow rate. Any liquid that is vaporized within tank 32 may be passed out from tank 32 through valve 33 in line 34 and combined with first column feed stream 13 and then into column 9.

Partially regenerated wash liquid or first column bottom liquid which may comprise low volatility fluorine compounds is removed from the bottom of first rectification column 24 in stream 35 through valve 36 and passed as second column feed into second rectification column 37 which is driven by external heat input through heat input line 38. Within second rectification column 37 the second column feed is separated by rectification into second column top vapor purified wash fluid and second column bottom liquid fluid which may comprise low volatility fluorine compounds.

Second column top vapor is removed from second rectification column 37 as stream 39 and passed to heat exchanger 12, where it is condensed and subcooled to a temperature below 100 K and preferably between 91 and 93 K by indirect heat exchange with vaporizing liquid cryogen stream 15. In an alternative embodiment, vapor stream 39 may be condensed by being passed through heat exchanger 2 prior to being subcooled in heat exchanger 12. The resultant liquid stream 40 is then divided into two streams, one of which is passed as reflux stream 41 to the top of second rectification column 37, and the other of which comprises wash liquid stream 10 which is passed into the upper portion of the wash column 9.

Second column bottom liquid in stream 42 which may comprise low volatility fluorine compounds is removed from the bottom of second rectification column 37, and passed out of the system and, if desired, recovered. This stream may be further processed for separation into refined components.

Liquid comprising high volatility fluorine compounds is periodically transferred from batch storage tank 32 through line 43 into the sump of third or batch column 44, which is driven by heat input to reboiler heat exchanger 45, and heat removal from condenser heat exchanger 46. The batch column is operated to separate the high volatility fluorine compound mixture into one or more refined product fractions. When more than one fluorine compound is to be recovered the refined products, and in certain cases close-boiling liquid mixtures, are sequentially removed as vapor or liquid fractions through valve 47 and line 48. The several streams, starting with the most volatile of the fluorine compounds and proceeding to compounds having lower volatility, are removed as products and directed to systems appropriate for further handling.

Valve 49 remains closed during most of the batch operation sequence. Following removal of the desired product streams from the top of the column, a small amount of residual liquid may be drained through valve 49 and line 50, by which it is removed from the system. Line 51 and valve 52 are provided to allow recycle of third column top vapor fractions having mixed fluorine compound composition to the wash column, if this is advantageous during any part of the batch column operation. During periods of operating of batch column 44, heat is supplied to reboiler 45 and removed from condenser 46 by a closed cycle vapor recompression heat pumping system. Low pressure stream 53, comprising a commercial refrigerant, is compressed in compressor 54, passed through heat exchanger 55, and then condensed in heat exchanger 45 to supply the reboiler heat requirement of batch column 44. The resultant liquefied refrigerant stream 56 is subcooled in heat exchanger 57, and then passed through valve 58 into heat exchanger 46, where the stream is vaporized to remove heat from the condenser of the batch column. Resultant vapor stream 59 is passed through heat exchangers 57 and 55. The warmed stream reconstitutes stream 53.

Figure 2:
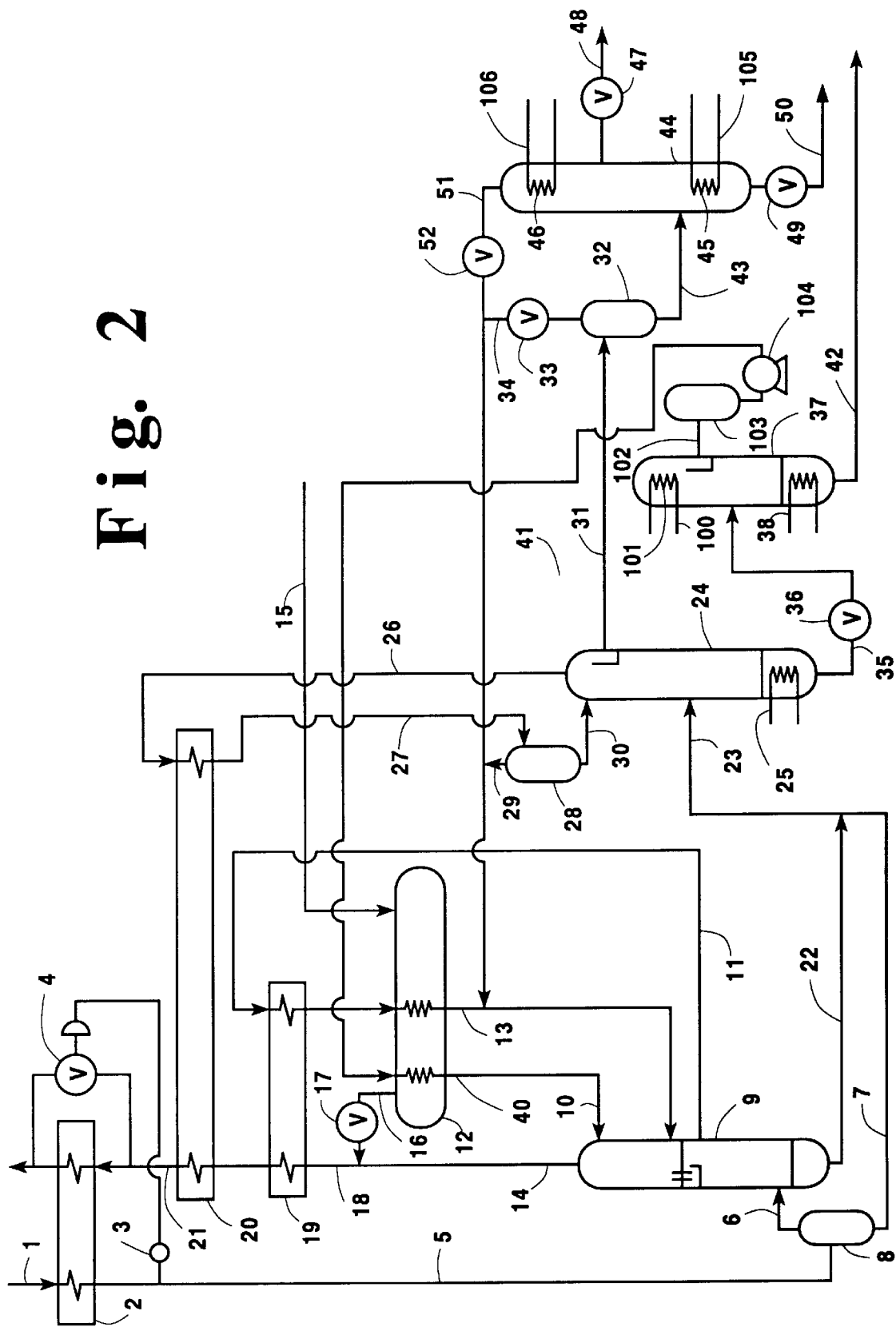
FIG. 2 is a schematic flow diagram of another embodiment of the fluorine compound recovery system of this invention employing additional heat input and refrigeration supply from external sources.

FIG. 2 illustrates another embodiment of the invention herein heat supply and removal from the rectification columns utilizes additional external sources. The numerals in FIG. 2 correspond to those of FIG. 1 for the common elements and these common elements will not be described again in detail. In the embodiment illustrated in FIG. 2, heat is removed at the top of second rectification column 37 by supply of an external refrigerant through line 100 to condenser heat exchanger 101. This results in total condensation of vapor at the top of column 37. Some of the resultant liquid flows down the column as reflux. A portion of the liquid is removed from the top of the column through line 102 and passed to holding tank 103, from which it is subsequently passed to pump 104 and then to heat exchanger 12, where it is subcooled at least to 100 K, and then passed as wash liquid stream 10 to wash column 9.

With respect to batch column 44, the supply of heat to reboiler 45 is by means of an external heat input through external heat input line 105. Similarly, removal of heat from condenser heat exchanger 46 is by means of external refrigeration input through refrigeration input line 106.

Those skilled in the art will recognize that the wash column can be replaced as the mass transfer device by a dephlegmator.

Now by the use of the cryogenic fluorine compound recovery system of this invention employing wash fluid recycle, one can effectively and efficiently recover fluorine compounds with lower energy consumption and with the need for less wash liquid than that required with presently available systems. Although the invention has been described in detail with reference to certain embodiments, those skilled in the art will recognize that there are other embodiments of the inventions within the spirit and the scope of the claims.

I claim:

1. A method for recovering fluorine compounds comprising:

(A) passing gaseous feed comprising carrier gas and high volatility fluorine compounds into a mass transfer contacting device, and passing wash liquid into the mass transfer contacting device;

(B) passing high volatility fluorine compounds into the wash liquid within the mass transfer contacting device to produce vapor comprising carrier gas and wash liquid comprising high volatility fluorine compounds;

(C) passing the wash liquid comprising high volatility fluorine compounds into a first rectification column as first column feed and separating the first column feed within said first rectification column by cryogenic rectification into top fluid comprising high volatility fluorine compounds and first column bottom fluid;

(D) passing first column bottom fluid comprising low volatility fluorine compounds into a second rectification column as second column feed, separating the second column feed by cryogenic rectification into second column top fluid and into second column bottom fluid, and passing second column top fluid into the mass transfer contacting device as wash liquid;

(E) passing top fluid comprising high volatility fluorine compounds into a third rectification column as third column feed and separating the third column feed by cryogenic rectification into third column top vapor and product high volatility fluorine compounds; and (F) recovering high volatility fluorine compounds from the third rectification column.

2. The method of claim 1 further comprising passing top fluid from the first rectification column into the mass transfer contacting device.

3. The method of claim 1 further comprising passing third column top vapor into the mass transfer contacting device.

4. The method of claim 1 wherein the gaseous feed additionally comprises low volatility fluorine compounds, further comprising recovering second column bottom fluid comprising low volatility fluorine compounds.

5. Apparatus for the recovery of fluorine compounds comprising:

(A) a mass transfer contacting device and means for passing fluorine compound-containing feed into the mass transfer contacting device;

(B) a first rectification column and means for passing fluid from the mass transfer contacting device into the first rectification column;

(C) a second rectification column and means for passing fluid from the lower portion of the first rectification column into the second rectification column;

(D) means for passing fluid from the upper portion of the second column into the mass transfer contacting device;

(E) a third rectification column and means for passing fluid from the upper portion of the first rectification column into the third rectification column; and (F) means for recovering fluorine compound product from the upper portion of the third rectification column.

6. The apparatus of claim 5 further comprising passing fluid from the upper portion of the first rectification column into the mass transfer contacting device.

7. The apparatus of claim 5 further comprising passing fluid from the upper portion of the third rectification column into the mass transfer contacting device.

8. The apparatus of claim 5 further comprising recovering fluid from the lower portion of the second rectification column.

* * * * *